(12) United States Patent
Lawson et al.

(10) Patent No.: US 8,304,200 B2
(45) Date of Patent: Nov. 6, 2012

(54) METHODS FOR OBTAINING ANTIBODIES

(75) Inventors: Alastair David Griffiths Lawson, Slough Berkshire (GB); Meryn Ruth Griffiths, Slough Berkshire (GB)

(73) Assignee: Celltech R&D Limited, Berkshire (GB)

( * ) Notice: Subject to any disclaimer, the term of this patent is extended or adjusted under 35 U.S.C. 154(b) by 596 days.

(21) Appl. No.: 12/387,153

(22) Filed: Apr. 28, 2009

(65) Prior Publication Data

US 2009/0275056 A1 Nov. 5, 2009

Related U.S. Application Data

(63) Continuation of application No. 10/568,246, filed as application No. PCT/GB2004/003523 on Aug. 12, 2004, now abandoned.

(30) Foreign Application Priority Data

Aug. 20, 2003 (GB) .................................. 0319587.2
Feb. 6, 2004 (GB) .................................. 0402641.5

(51) Int. Cl.
*G01N 33/53* (2006.01)
(52) U.S. Cl. ...................................................... 435/7.21
(58) Field of Classification Search ........................ None
See application file for complete search history.

(56) References Cited

U.S. PATENT DOCUMENTS 5,213,960 A * 5/1993 Chang ................................ 435/2
5,326,696 A 7/1994 Chang

FOREIGN PATENT DOCUMENTS

| WO | WO 92/02551 | 2/1992 |
| WO | WO 94/09117 | 4/1994 |
| WO | WO 03/012449 | 2/2003 |
| WO | WO 2004/051268 | 6/2004 |

OTHER PUBLICATIONS

Goldsby et al. (Kuby Immunology, 4th edition, 2000, W. H. Freeman and Co., New York, USA. pp. 104 and 165-169).*
Brezinsky, S. et al (2003) J. Immunol. Methods 277:141-155.
Holmes, P. et at (1999) J. Immunol. Methods 230:141-147.
Rodriguez-Carreno, M. et al (2002) J. Immunol. Methods 259:171-179.

* cited by examiner

*Primary Examiner* — Sharon Wen
(74) *Attorney, Agent, or Firm* — Klauber & Jackson LLC

(57) ABSTRACT

The invention is directed towards a method of enriching a population of cells in those cells that produce an antibody which recognizes an antigen of interest. In particular, an untagged antigen is used in conjunction with a polyclonal antibody to isolate cells recognizing said antigen.

5 Claims, 1 Drawing Sheet

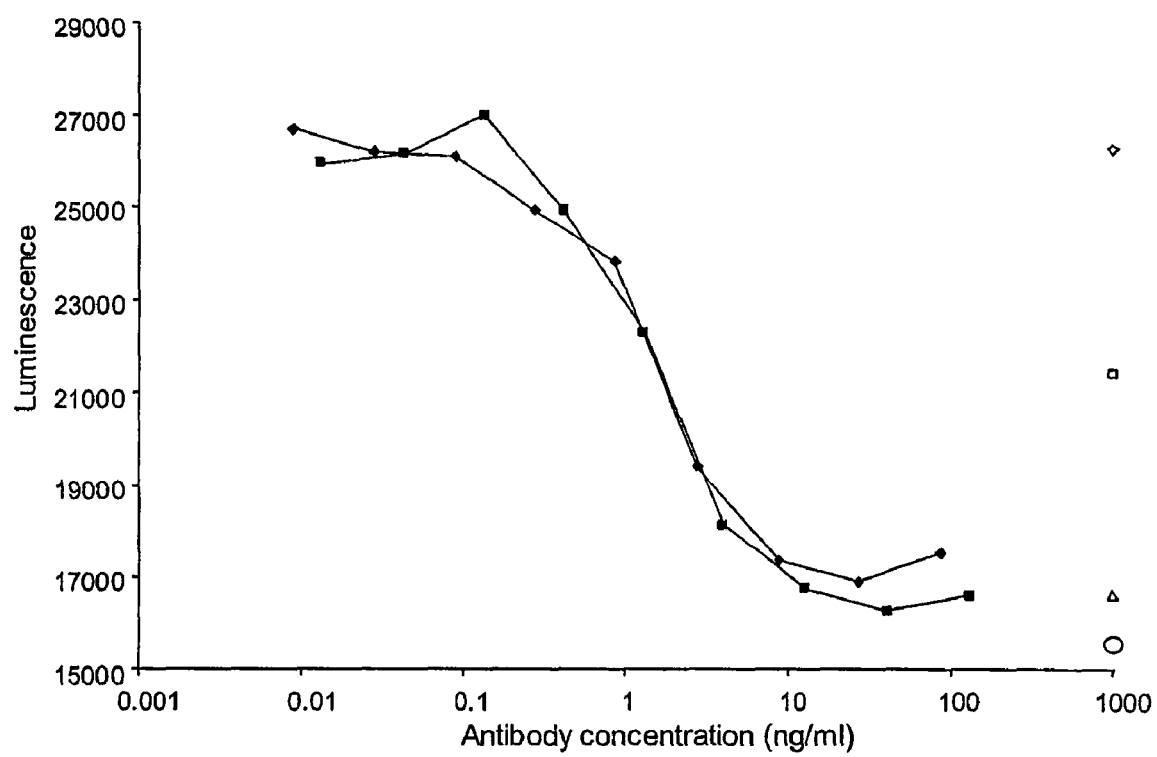

METHODS FOR OBTAINING ANTIBODIES

This application is a continuation of U.S. application, U.S. Ser. No. 10/568,246, filed Jul. 28, 2006, now abandoned.

The present invention relates to improved methods for the selection of cells producing antibodies specific for an antigen of interest.

Antibodies are a particular class of proteins which have been developed for therapeutic and diagnostic purposes. The isolation of cells producing antibody specific for an antigen of interest is historically performed using hybridoma technology. Other methods include isolating antibodies from bacterially expressed libraries which are limited by: (i) restrictions to the practical limits of the size of libraries; and (ii) the requirement for the antibody to be expressed and properly folded in bacteria. A number of alternative methods have been designed to enable high affinity antibodies generated during in vivo immune responses to be isolated from any species (Babcook et al., 1996, Proc. Natl. Acad. Sci, 93, 7843-7848; WO 92/02551; de Wildt et al., 1997, J. Inmunol. Methods, 207:61-67 and in Lagerkvist, et al., 1995, BioTechniques 18(5):862-869).

Methods for the detection and isolation of cells producing antibody specific for an antigen of interest are well-known in the art and include isolation of antibody producing cells by binding to biotinylated antigen and capture on streptavidin-beads, panning against antigen-coated plastic surfaces, rosetting with antigen-coated red blood cells, flow cytometric analysis and single cell sorting where the antigen is fluorescently labelled. The major drawback of these methods is that the presentation of antigen is generally random such that masking of the antigenic epitope, which is specifically recognised by the antibody producing, cell can occur. In particular, where the antigen of interest is a protein, the labelling of the antigen for example with a fluorescent label, is a chemical modification of the surface of the antigen that can decrease the affinity of an antibody-antigen interaction or prevent interaction. Where the antigens of interest are small proteins or short peptides the introduction of a chemical modification in the form of a label, such as a fluorescent label, may interfere such that little or no binding of antigen to specific antibody occurs.

Similar problems exist where the antigen of interest is provided tagged as a fusion protein. The incorporation of an additional sequence on the C-terminus or N-terminus of a protein can result in aberrant folding such that the antigen is not folded into a native conformation. As such, antigenic epitopes exposed within, for example, a host immunised with native antigen may not be accessible on a fusion protein of the same antigen. Thus, at the step of enrichment of cells producing antibody specific for the native antigen, those cells producing antibody to epitopes which are masked or altered in the fusion protein will not be detected and isolated.

Using unlabelled or untagged antigen is therefore particularly advantageous in that this avoids any modification of the antigen which can modify or mask interaction sites and which, in turn, can result in absence of detection of an antibody specific for the antigen of interest. Accordingly, provided is a method of enriching a population of cells in those cells which produce an antibody that recognises an antigen of interest, comprising:
a) bringing said population into contact with an antibody that recognises a marker which is essentially unique to those cells present in the population which are capable of producing an antibody, said antibody being attached to a first fluorescent label;
b) bringing said population into contact with the antigen of interest;
c) bringing said population into contact with a sample comprising an antibody that recognises said antigen, said antibody being attached to a second fluorescent label; and
d) separating from the population those cells which are detectable by virtue of being associated with the first and second fluorescent labels.

The terms 'cells which are capable of producing an antibody' or 'antibody producing cell' include any cell secreting an antibody, such as a B-lymphocyte, a plasma cell, a plasmablast, an activated B cell or a memory B cell. Such cells may produce antibody of any affinity, for example high affinity antibody or lower affinity antibody. The methods of the invention are not dependent on the affinity of the antibody produced by such cells. A population comprising antibody producing cells for use in the invention may be obtained from an animal which has either been immunized with an antigen of interest, or which has developed an immune response to an antigen as a result of disease. For example but without limitation, the population can comprise a peripheral blood cell sample, spleen cells or cells derived from a lymph node. Other populations comprising antibody producing cells for use in the present invention may include a population of hybridoma cells, a population comprising any transformed cell, and in particular, a population comprising any mammalian cells which express immunoglobulin genes or parts thereof. Examples of such mammalian cells include but are not limited to NS0, CHO, COS and 293 cells. In a preferred embodiment, the populations of antibody producing cells for use in the present invention produce a range of antibodies with different binding specificities. In another embodiment, the population of cells comprising at least one cell producing an antibody that recognises an antigen of interest is derived from several sources, for example but without limitation from several lymph nodes which may be from one or more animals. It will also be apparent that samples or populations of cells derived from two or more animals can be pooled for use in the methods of the invention. In a particular embodiment, the population of cells is derived from a human who has been exposed to an antigen of interest or who has developed an immune response to an antigen as a result of a disease or condition. In such a case, the sample comprising the population of cells for enrichment is preferably a peripheral blood sample or one or more lymph nodes.

Preferably, the population is suspended in an appropriate medium for use in the methods of the invention. An appropriate medium for the assay will be one that provides at least the minimum requirements for short-term maintenance of cellular integrity and cellular structures, such as an isotonic buffer. One example, but without limitation, is immune cell medium comprising Roswell Park Memorial Institute medium (RPMI)+10% foetal bovine serum; 50 µM 2-β-mercaptoethanol; 2 mM glutamine; 20 mM Hepes; and 1× Penicillin and Streptomycin. Under such conditions the antibody producing cells produce and secrete antibodies.

A population comprising antibody producing cells may be depleted of unwanted cells, such as for example but without limitation, red blood cells, T cells, macrophages or other cells if so desired. In the methods of the invention the population of cells provided, at least one of which is capable of producing an antibody, is preferably depleted of any red blood cells for example using centrifugation or red cell lysis as known in the art.

The term 'antibody' includes any recombinant or naturally occurring immunoglobulin molecule such as a member of the IgG class e.g. IgG1, including a monoclonal or polyclonal antibody, any antigen binding immunoglobulin fragment, such as Fv, Fab' and F(ab')$_2$ fragments, and any derivatives thereof, such as single chain Fv fragments. The term antibody that 'recognises an antigen' includes an antibody that binds to, or is specific for, an antigen of interest. Most preferably, an antibody binds to the antigen of interest and does not bind to or recognise other unrelated antigens.

In the methods of the invention, the antibody of part a) above recognises a marker which is essentially unique to those cells capable of producing an antibody, for example a marker essentially unique to B cells. 'Essentially unique' includes a marker that is predominantly present on those cells capable of producing antibody compared to other cells types, but not necessarily to the exclusion of all other cell types. Hence, such a marker may also be present on one or two or even three or more other cell types. Examples of preferred markers include without limitation, CD5, CD9, CD10, CD19, CD20, CD21, CD22, CD45, CD45 RC, although one skilled in the art will recognise that many of the 'CD' markers present on B cells can be used. In one example, the antibody of part a) above is a monoclonal antibody. Cells expressing a marker recognised by an antibody of part a) above will be distinguished by virtue of having the first label attached. Those cells that are not capable of producing antibody will be distinguished by being unlabelled or negative. In a further embodiment, those cells, within a population, which are capable of producing an antibody may be attached to two labels. In such a case, an antibody that recognises a second, different marker essentially unique to said cells is labelled with a third label, i.e. a label that is different from those which are attached to the antibodies of parts a) and b), above. Those antibody producing cells within the population provided will thus be distinguished by having two labels attached. Thus, the selection of those cells which carry the chosen markers is made possible by distinguishing from those which carry only one marker, or no marker in which case said cells will be unlabelled or negative.

In the methods of the invention, the antibody of part b) above is most preferably a polyclonal antibody that is from the same source as that of the population of cells for enrichment. In a preferred example, the source of the population of cells is an animal immunised with an untagged antigen of interest and the polyclonal antibody is prepared from a sample of blood from said immunised animal. In another embodiment, the antibody of part b) above is present in a pool of polyclonal sera; for example it is present in a pool of sera from at least two animals which have been immunised with the antigen of interest. It will be apparent to one skilled in the art that the polyclonal antibody may be present as a serum sample, but is more preferably prepared as an IgG fraction. Methods for producing an IgG fraction are well known in the art and include affinity chromatography such as Protein A or Protein G affinity chromatography, and ammonium sulphate or caprylic acid precipitation. The polyclonal antibody may be a whole IgG or a fragment thereof such as a Fab', F(ab')$_2$ or Fab fragment. Fragments may be produced using any method known in the art, for example using papain or pepsin digestion. In an alternative embodiment, the antibody of part b) above is a monoclonal antibody.

Labels of use in the methods of the invention are fluorescent labels. Appropriate fluorescent labels are well known in the art, as are methods for performing the labelling of antibodies with such labels. Such labels can include, but are not limited to, Alexa Fluor 488, R-phycoerythrin, Aqua, Texas-Red, FITC, rhodamine, a rhodamine derivative, fluorescein, a fluorescein derivative, cascade blue, Cy5 or Cy3. Preferably, the first or second fluorescent label is Alexa Fluor 488 or R-phycoerythrin. It is understood that the first and second labels, and any subsequent labels, if used, are different labels. In a preferred embodiment, the methods of the invention utilise two labels, i.e. a first and second fluorescent label. Labelled antibodies are preferably used at, for example but without limitation, 1-5 µg/ml and incubation of such antibodies with a cell sample is preferably performed in the cold for an appropriate length of time, for example 60 mins. It will be apparent to one skilled in the art that the concentration of antibody may be less or more than the stated values, above, and hence may range from, for example 0.1 µg/ml or less to 10 µg/ml or more.

In the methods of the invention the antigen is provided in an untagged form. The term 'antigen' includes any substance that can be recognised by an antibody, including proteins, glycoproteins and carbohydrates. Preferably these antigens include biologically active proteins, such as hormones, cytokines, and their cell surface receptors, bacterial or parasitic cell membranes or purified components thereof, and viral antigens. In a particular embodiment, the antigen is presented on the surface of a cell. Such an antigen may be endogenous or recombinant. Most preferably, the antigen is available in a pure form obtained either by direct purification from the native source or by recombinant expression and purification of said antigen. A pure form includes antigens that are at least 75%, 80%, 85% or 90% free from contaminants, and preferably at least 95% or 99% free from contaminants. Most preferably, antigens are 100% pure or have no detectable contaminants. In one embodiment, the antigen is expressed recombinantly as a fusion protein and the fusion tag has been removed prior to use of the antigen. Removal of such tags is well known in the art and such removal may leave a small number of residual amino acid residues which are not normally present at the N-terminus or C-terminus of the antigen in its native state, e.g. residues from a linker region and/or the region of cleavage of the tag. Thus, the term 'untagged' antigen includes antigens which have had a tag removed regardless of whether or not additional amino acid residues remain attached to the antigen as a result of the cleavage. Examples of such tags are known in the art and expression vectors incorporating nucleic acid code for such tags are commercially available for example, but not limited to, myc, FLAG or H is tags.

Preferably, incubation of the antigen at a concentration of approximately 1 µM to 1 pM in the presence of a population of, for example but without limitation, approximately $10^7$ or $10^8$ white blood cells some of which are capable of producing antibody is performed on ice for approximately 60 min. It is understood that the number of cells may be less or more than $10^7$, and may be $10^6$, $10^5$, $10^4$ or less, or $10^9$ or more as desired. The concentration of antigen may also be varied and may be chosen as appropriate and understood by one skilled in the art. In one embodiment, low concentrations of antigen can be used to bias towards selecting B cells that produce high affinity antibody.

In a preferred embodiment, parts a), b), and c) are performed simultaneously, the first and second labels are fluorescent labels and the performance is optionally followed by at least one wash step. In another embodiment parts a) and b), or a) and c), or b) and c), are performed simultaneously and optionally comprise at least one wash step. Wash steps may be performed by any means known in the art, for example using phosphate buffered saline (PBS) or other appropriate media. The population of cells may be separated from any incubation or wash media using, for example but without limitation, centrifugation. Alternatively, cells may be left to settle under gravity followed by removal of the washing buffer or other media.

In another embodiment, parts a), b) and c) are performed consecutively, in any order, such that the performance of part a) may be followed by the performance of part b), and then part c). It will be apparent to a person skilled in the art that any permutation is possible, e.g. part a), then part c) followed by part b), or part b) then part a) followed by part c), etc. It will also be apparent that one or more washing steps as described above may be carried out after the performance of any of parts a) to d) or combination thereof.

In the methods of the invention, separation of those cells that are attached to both a first and a second label from a population of cells is most preferably performed using fluorescence activated cell sorting (FACS). Alternatively, said cells are identified using a fluorescence microscope. Cells identified using the latter method may be isolated by micromanipulation. Thus, an enriched population of cells producing an antibody that recognises an antigen of interest can be prepared using the methods of the invention. In one preferred embodiment, the enriched population of cells is subject to at least one washing step. Alternatively, the enriched population of cells is not washed.

An enriched population of cells obtained using any of the methods of the invention may be further separated, if desired, to obtain and clone one or more single antibody producing cells using any method known in the art. Methods to obtain and clone single antibody producing cells include methods such as, but not limited to, the selected lymphocyte antibody method (SLAM) described in WO 92/02551 and Babcook et al., 1996, Proc. Natl. Acad. Sci USA 93:7843-7848. Other techniques include those described by de Wildt et al., 1997, J. Immunol. Methods, 207:61-67 and Lagerkvist et al., 1995, BioTechniques 18(5):862-869. The above methods rely on the isolation of individual antibody producing cells which are then clonally expanded, followed by screening for those clones which are producing an antibody that recognises an antigen of interest, and, if desired, the subsequent identification of the sequence of their variable heavy ($V_H$) and light ($V_L$) chain genes.

Alternatively, the enriched population of cells producing antibody that recognises an antigen of interest may be plated into one or more wells and screened for antibody production followed sequence identification, if desired, as above. In such a case, the enriched population of cells is divided such that a plurality of cells is placed in the well for culture. It is preferred that the wells are seeded with between 2 and 100 B cells; more preferably with between 2 and 75 B cells; more preferably between 5 and 50 B cells; more preferably between 5 and 25 B cells; more preferably between 5 and 15 B cells; more preferably between 8 and 12 B cells; yet more preferably about 10 B cells/well.

In one embodiment, the B cells are cultured for about, or at least, 4, 5, 6, 7, 8, 9 or 10 days or up to one month. Preferably, the B cells are cultured for about 5 to 10 days, more preferably for about 6 to 9, or 6 to 8 days.

Most preferably, the cells are cultured under conditions suitable for the clonal expansion of the B cells. Clonal expansion results in a greater quantity of antibody being produced and higher levels of mRNA expression. Clonal expansion is preferably performed in the presence of an antigen to which the antibody with the desired function binds which may assist in the isolation of higher affinity antibodies via in vitro affinity maturation.

Conditions suitable for the clonal expansion of B cells are well known in the art. Important conditions include the culture medium, the time for which the cells are cultured, temperature and atmospheric $CO_2$.

Preferably, the B cells are cultured with irradiated EL-4 cells in T cell conditioned media. More preferably, the B cells are cultured with irradiated mutant murine EL-4 thymoma cells, EL-4/B5, in conjunction with human T-cell/macrophage supernatant as a source of proliferation and differentiation factors. The EL-4/B5 cells activate the B-cells via a MHC-nonrestricted direct cell-cell interaction. The activation signal itself is not mitogenic but sensitizes the B cells to respond to one (IL-2) or several cytokines present in human T-cell supernatant.

Once the cells have been cultured, a plurality of the cultured cells may be screened to ascertain the presence of cells capable of producing an antibody having the desired function. Preferably, this involves screening the culture supernatant of said plurality of cultured cells. Where cells have been cultured in a series of wells, the wells can be individually assayed (e.g. by taking culture supernatant from the wells) for the presence of cells capable of producing an antibody recognising the antigen of interest to thereby identify one or more wells which are positive for the presence of cells capable of producing an antibody having the desired function. Said antibodies can then be obtained from a positive well. The antibodies can be synthesized directly or indirectly from the cells present in the well.

Accordingly, provided is a method of enriching a population of cells in those cells which produce an antibody that recognises an antigen of interest, comprising:
a) bringing said population into contact with an antibody that recognises a marker which is essentially unique to those cells present in the population which are capable of producing an antibody, said antibody being attached to a first fluorescent label;
b) bringing said population into contact with the antigen of interest;
c) bringing said population into contact with a sample comprising an antibody that recognises said antigen, said antibody being attached to a second fluorescent label;
d) separating from the population those cells which are detectable by virtue of being associated with the first and second fluorescent labels;
e) culturing a plurality of those cells associated with the antigen-antibody-particle complex;
f) screening the cultured cells to identify those cells capable of producing an antibody which recognises an antigen of interest; and
g) isolating said antibody directly or indirectly from the cells.

Screening for cells producing antibodies recognising the antigen of interest may be performed by any means known in the art, such as by enzyme-linked immunosorbent assay (ELISA) or by screening for a functional activity such as neutralisation of antigen activity, or antagonistic or agonistic activities. Such assays are known in the art, for example, functional screening of receptor/ligand binding. Antibodies may be selected based on binding affinities such as, for example, may be determined using a BIAcore machine, or using a competitive radioimmunoassay.

The desired antibody, i.e. the antibody recognising the antigen of interest, may be isolated directly or indirectly from the cultured cells or from descendants thereof. Direct isolation can be achieved by purification of secreted antibody from the clonal culture supernatant using standard, well known techniques. Alternatively, indirect isolation is performed. Such antibodies are synthesised by isolating the $V_L$ and $V_H$ chain gene regions or the entire genes may be cloned and used to produce recombinant antibodies that recognise the antigen of interest.

Such antibodies can include functionally active fragments, derivatives or analogues and may be, but are not limited to, bi-, tri- or tetra-valent antibodies, humanized or chimeric antibodies, single chain antibodies, Fab fragments, Fab' and F(ab')$_2$ fragments, fragments produced by a Fab expression library, anti-idiotypic (anti-Id) antibodies, epitope-binding fragments and derivatives of any of the above, e.g. single chain FV fragments. Humanized antibodies are antibody molecules from non-human species having one or more complementarity determining regions (CDRs) from the non-human species and a framework region from a human immunoglobulin molecule (see, e.g. U.S. Pat. No. 5,585,089). The methods for creating these antibody molecules are well known in the art (see for example, Boss et al., U.S. Pat. No. 4,816,397; Cabilly et al., U.S. Pat. No. 6,331,415; Shrader et al., WO 92/02551; Ward et al., 1989, Nature, 341, 544; Orlandi et al., 1989, Proc. Natl. Acad. Sci. USA, 86, 3833; Riechmann et al., 1988, Nature, 322, 323; Bird et al, 1988, Science, 242, 423; Queen et al., U.S. Pat. No. 5,585,089; Adair, W091/09967; Mountain and Adair, 1992, Biotechnol. Genet. Eng. Rev, 10, 1-142).

Chimeric antibodies are those antibodies encoded by immunoglobulin genes that have been genetically engineered so that the light and heavy chain genes are composed of immunoglobulin gene segments belonging to different species. These chimeric antibodies are likely to be less antigenic. Bivalent antibodies may be made by methods known in the art (Milstein et al., 1983, Nature 305:537-539; WO 93/08829, Traunecker et al., 1991, EMBO J. 10:3655-3659). Bi-, tri- and tetra-valent antibodies may comprise multiple specificities or may be monospecific (see for example WO 92/22853).

The types of expression systems available to produce these antibody molecules include bacterial, yeast insect and mammalian expression systems, the methods for which are well known in the art (Verma et al., 1998, Journal of Immunological Methods, 216, 165-181). Techniques for the production of single chain antibodies, such as those described in U.S. Pat. No. 4,946,778 can also be adapted to produce single chain antibodies to the antigen of interest. Also, transgenic mice or other organisms, including other mammals, may be used to express humanized antibodies.

Antibodies obtained using the above methods may be used without further modification, or if desired following modification including conjugation to one or more reporter or effector molecules, for any suitable diagnostic or therapeutic purpose. An antibody, optionally conjugated to a therapeutic moiety, can be used therapeutically alone or in combination with a cytotoxic factor(s) and/or cytokine(s). In particular, antibodies can be conjugated to a therapeutic agent, such as a cytotoxic agent, a radionuclide or drug moiety to modify a given biological response. The therapeutic agent is not to be construed as limited to classical chemical therapeutic agents. For example, the therapeutic agent may be a drug moiety which may be a protein or polypeptide possessing a desired biological activity. Such moieties may include, for example and without limitation, a toxin such as abrin, ricin A, pseudomonas exotoxin, or diphtheria toxin, a protein such as tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), interleukin-6 (IL-6), granulocyte macrophage colony stimulating factor (GM-CSF), granulocyte colony stimulating factor (G-CSF), nerve growth factor (NGF) or other growth factor.

Therapeutic agents also include cytotoxins or cytotoxic agents including any agent that is detrimental to (e.g. kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other therapeutic moieties may include radionuclides such as $^{111}$In and $^{90}$Y, Lu$^{177}$, Bismuth$^{213}$, Californium$^{252}$, Iridium$^{192}$ and Tunsten$^{188}$/Rhenium$^{188}$; or drugs such as but not limited to, alkylphosphocholines, topoisomerase I inhibitors, taxoids and suramin.

Techniques for conjugating such therapeutic agents to antibodies are well known in the art (see, e.g. Arnon et al., "Monoclonal Antibodies For Immunotargeting Of Drugs In Cancer Therapy", in Monoclonal Antibodies And Cancer Therapy, Reisfeld et al., eds., 1985 pp. 243-56, ed. Alan R. Liss, Inc; Hellstrom et al., "Antibodies For Drug Delivery", in Controlled Drug Delivery, 2nd Ed., Robinson et al., eds., 1987, pp. 623-53, Marcel Dekker, Inc.; Thorpe, "Antibody Carriers Of Cytotoxic Agents In Cancer Therapy: A Review", in Monoclonal Antibodies '84: Biological And Clinical Applications; Pinchera et al., 1985, eds., pp. 475-506; "Analysis, Results, And Future Prospective Of The Therapeutic Use Of Radiolabelled Antibody In Cancer Therapy", in Monoclonal Antibodies For Cancer Detection And Therapy, Baldwin et al. (eds.), 1985, pp. 303-16, Academic Press; Thorpe et al., 1982 "The Preparation And Cytotoxic Properties Of Antibody-Toxin Conjugates", Immunol. Rev., 62:119-58 and Dubowchik et al., 1999, Pharmacology and Therapeutics, 83, 67-123).

The antibodies for use in the invention include analogues and derivatives that are modified, for example but without limitation, by the covalent attachment of any type of molecule. Preferably, said attachment does not impair immunospecific binding. In one aspect, an antibody can be conjugated to a second antibody to form an antibody heteroconjugate (see U.S. Pat. No. 4,676,980).

In other embodiments, the invention provides the therapeutic use of fusion proteins of the antibodies (or functionally active fragments thereof), for example but without limitation, where the antibody or fragment thereof is fused via a covalent bond (e.g. a peptide bond), at optionally the N-terminus or the C-terminus, to an amino acid sequence of another protein (or portion thereof; preferably at least a 10, 20 or 50 amino acid portion of the protein). Preferably the antibody, or fragment thereof, is linked to the other protein at the N-terminus of the constant domain of the antibody. In another aspect, an antibody fusion protein may facilitate depletion or purification of a polypeptide as described herein, increase half-life in vivo, and enhance the delivery of an antigen across an epithelial barrier to the immune system.

Where the fusion protein is an antibody fragment linked to an effector or reporter molecule, this may be prepared by standard chemical or recombinant DNA procedures. For instance, it may have a macrocycle for chelating a heavy metal atom, or a toxin, such as ricin, attached to it by a covalent bridging structure. A preferred effector group is a polymer molecule, which may be attached to the modified Fab fragment to increase its half-life in vivo.

The polymer molecule may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Particular optional substituents which may be present on the above-mentioned synthetic polymers include one or more hydroxy, methyl or methoxy groups. Particular examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Particular naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, preferably from 5000 to 40000 Da and more preferably from 25000 to 40000 Da. The polymer size may in particular be selected on the basis of the intended use of the product. Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 25000 Da to 40000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 25000 Da to about 40000 Da.

Each polymer molecule attached to the modified antibody fragment may be covalently linked to the sulphur atom of a cysteine residue located in the fragment. The covalent linkage will generally be a disulphide bond or, in particular, a sulphur-carbon bond.

Where desired, the antibody fragment may have one or more effector or reporter molecules attached to it. The effector or reporter molecules may be attached to the antibody fragment through any available amino acid side-chain or terminal amino acid functional group located in the fragment, for example any free amino, imino, hydroxyl or carboxyl group.

An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

Standard chemical or recombinant DNA procedures in which the antibody fragment is linked either directly or via a coupling agent to the effector or reporter molecule either before or after reaction with the activated polymer as appropriate may be used. Particular chemical procedures include, for example, those described in WO 93/06231, WO 92/22583, WO 90/09195, WO 89/01476, WO 99/15549 and WO 03/031581. Alternatively, where the effector or reporter molecule is a protein or polypeptide the linkage may be achieved using recombinant DNA procedures, for example as described in WO 86/01533 and EP 0392745.

Most preferably antibodies are attached to poly(ethyleneglycol) (PEG) moieties. Preferably, a modified Fab fragment is PEGylated, i.e. has PEG (poly(ethyleneglycol)) covalently attached thereto, e.g. according to the method disclosed in EP 0948544 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one embodiment, a PEG modified Fab fragment has a maleimide group covalently linked to a single thiol group in a modified hinge region. A lysine residue may be covalently linked to the maleimide group. To each of the amine groups on the lysine residue may be attached a methoxypoly(ethyleneglycol) polymer having a molecular weight of approximately 20,000 Da. The total molecular weight of the entire effector molecule may therefore be approximately 40,000 Da.

Antibodies isolated directly or indirectly according to the methods of the invention are useful in diagnosis. Thus, provided is a method of screening for and/or diagnosis or prognosis of a disease in a subject, and/or monitoring the effectiveness of therapy for said disease, which comprises the step of detecting and/or quantifying in a biological sample obtained from said subject, the expression of an antigen recognised by an antibody isolated according to the methods of the invention. In particular, the step of detecting comprises contacting the sample with the antibody and detecting whether binding has occurred between the antibody and the antigen in the sample.

Repertoires of such antibodies, or fragments thereof, are also useful in bacteriophage libraries.

Antibodies prepared directly or indirectly as a result of using the methods of the invention also find use in the treatment and/or prophylaxis of a disease or condition depending on the antigen of interest selected. For example but without limitation, an antigen restricted to expression on the surface of tumour cells may be selected for immunisation of one or more animals. Accordingly, in a further aspect, the invention includes an antibody or fragment thereof isolated according to any one of the methods described, above. In one embodiment, such antibodies are humanised (see, for example, Adair et al., 1992, Immunol Rev. 130:540 and WO 91/09967). Therefore, according to the invention provided is the use of an antibody prepared using the methods of the invention for the manufacture of a medicament for the treatment and/or prophylaxis of a condition or disease associated with aberrant expression or aberrant activity of the antigen of interest, i.e. recognised by an antibody identified using the methods of the invention. Also provided is a method for the treatment and/or prophylaxis of a disease associated with aberrant expression or aberrant activity of an antigen recognised by an antibody isolated according to the methods of the invention comprising administering a therapeutically effective amount of a composition comprising said antibody. Such a disease or condition includes cancers, autoimmune disorders or inflammatory disorders. For such use the antibodies will generally be administered in the form of a pharmaceutical composition.

Thus, according to the invention there is provided a pharmaceutical composition comprising an antibody that recognises an antigen of interest and a pharmaceutically acceptable diluent, excipient and/or carrier.

When a reference is made herein to a method of treating or preventing a disease or condition using a particular antibody or combination of antibodies, it is to be understood that such a reference is intended to include the use of that antibody or combination of antibodies in the preparation of a medicament for the treatment and/or prophylaxis of the disease or condition.

The composition will usually be supplied as part of a sterile, pharmaceutical composition that will normally include a pharmaceutically acceptable carrier. This composition may be in any suitable form (depending upon the desired method of administering it to a patient).

Antibodies of the invention may be administered to a subject by any of the routes conventionally used for drug administration, for example they may be administered parenterally, orally or by inhalation. The most suitable route for administration in any given case will depend on the particular antibody, the disease or condition involved, the subject, and the nature and severity of the disease or condition and the physical condition of the subject.

The antibodies may be administered in combination, e.g. simultaneously, sequentially or separately, with one or more other therapeutically active compounds, e.g. anti-tumour or anti-inflammatory compounds.

Pharmaceutical compositions may be conveniently presented in unit dose forms containing a predetermined amount of an antibody of the invention per dose. Such a unit may contain for example but without limitation, 750 mg/kg to 0.1 mg/kg depending on the condition being treated, the route of administration and the age, weight and condition of the subject.

Pharmaceutically acceptable carriers for use in the invention may take a wide variety of forms depending, e.g. on the route of administration.

Compositions for oral administration may be liquid or solid. Oral liquid preparations may be in the form of, for example, aqueous or oily suspensions, solutions, emulsions, syrups or elixirs, or may be presented as a dry product for reconstitution with water or other suitable vehicle before use. Oral liquid preparations may contain suspending agents as known in the art.

In the case of oral solid preparations such as powders, capsules and tablets, carriers such as starches, sugars, microcrystalline cellulose, diluents, granulating agents, lubricants, binders, disintegrating agents, and the like may be included. Because of their ease of administration, tablets and capsules represent the most advantageous oral dosage unit form in which case solid pharmaceutical carriers are generally employed. In addition to the common dosage forms set out above, antibodies of the invention may also be administered by controlled release means and/or delivery devices. Tablets and capsules may comprise conventional carriers or excipients such as binding agents for example, syrup, acacia, gelatin, sorbitol, tragacanth, or polyvinylpyrrolidone; fillers, for example lactose, sugar, maize-starch, calcium phosphate, sorbitol or glycine; tableting lubricants, for example magnesium stearate, talc, polyethylene glycol or silica; disintegrants, for example potato starch; or acceptable wetting agents such as sodium lauryl sulphate. The tablets may be coated by standard aqueous or non-aqueous techniques according to methods well known in normal pharmaceutical practice.

Pharmaceutical compositions of the present invention suitable for oral administration may be presented as discrete units such as capsules, cachets or tablets, each containing a predetermined amount of the antibody, as a powder or granules, or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the antibody with the carrier, which constitutes one or more necessary ingredients. In general, the compositions are prepared by uniformly and intimately admixing the antibody with liquid carriers or finely divided solid carriers or both, and then, if necessary, shaping the product into the desired presentation. For example, a tablet may be prepared by compression or moulding, optionally with one or more accessory ingredients.

Pharmaceutical compositions suitable for parenteral administration may be prepared as solutions or suspensions of the antibodies of the invention in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include aqueous or non-aqueous sterile injection solutions which may contain anti-oxidants, buffers, bacteriostats and solutes which render the composition isotonic with the blood of the intended recipient, and aqueous and non-aqueous sterile suspensions which may include suspending agents and thickening agents. Extemporaneous injection solutions, dispersions and suspensions may be prepared from sterile powders, granules and tablets.

Pharmaceutical compositions can be administered with medical devices known in the art. For example, in a preferred embodiment, a pharmaceutical composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system.

Many other such implants, delivery systems, and modules are known to those skilled in the art.

In certain embodiments, the pharmaceutical compositions of the invention can be formulated to ensure proper distribution in vivo. For example, the blood-brain barrier excludes many highly hydrophilic compounds and it may be preferable to deliver pharmaceutical compositions in liposomes. Thus, in one embodiment of the invention, the antibodies of the invention are formulated in liposomes; in a more preferred embodiment, the liposomes include a targeting moiety. In a most preferred embodiment, the therapeutic compounds in the liposomes are delivered by bolus injection to a site proximal to the problem area, e.g. proximal to a tumour. For methods of manufacturing liposomes, see, e.g. U.S. Pat. Nos. 4,522,811; 5,374,548; and 5,399,331. The liposomes may comprise one or more moieties which are selectively transported into specific cells or organs, thus enhancing targeted drug delivery (see, e.g. Ranade, V V. 1989, J. Clin. Pharmacol. 29:685). Exemplary targeting moieties include folate or biotin (see, e.g. U.S. Pat. No. 5,416,016.); mannosides (Umezawa et al., 1988, Biochem. Biophys. Res. Commun. 153:1038); antibodies (Bloeman, P G. et al, 1995, FEBS Lett. 357:140; M. Owais et al., 1995, Antimicrob. Agents Chemother. 39:180); surfactant protein A receptor (Briscoe et al., 1995, Am. J. Physiol. 1233:134), different species of which may comprise the formulations of the inventions, as well as components of the invented molecules; p120 (Schreier et al., 1994, J. Biol. Chem. 269:9090); see also Keinanen, K. & Laukkanen, M L. 1994, FEBS Lett. 346:123; Killion, J J. & Fidler, I J. 1994, Immunomethods 4:273. The compositions may be presented in unit-dose or multi-dose containers, for example in sealed ampoules and vials and to enhance stability, may be stored in a freeze-dried (lyophilized) condition requiring only the addition of the sterile liquid carrier, for example water for injections, immediately prior to use. The sterile liquid carrier may be supplied in a separate vial or ampoule and can be a solvent or dispersion medium containing, for example, water, ethanol, polyol (e.g. glycerol, propylene glycol and liquid polyethylene glycol), suitable mixtures thereof, and vegetable oils. Advantageously, agents such as a local anaesthetic, preservative and buffering agents can be included in the sterile liquid carrier.

The dosage to be administered of an antibody will vary according to the particular antibody, the disease or condition involved, the subject, and the nature and severity of the disease and the physical condition of the subject, and the selected route of administration; the appropriate dosage can be readily determined by a person skilled in the art. For the treatment and/or prophylaxis of a disease or condition in humans and animals pharmaceutical compositions comprising antibodies can be administered to patients (e.g., human subjects) at therapeutically or prophylactically effective dosages (e.g. dosages which result in tumour growth inhibition and/or tumour cell migration inhibition) using any suitable route of administration, such as injection and other routes of administration known in the art for antibody-based clinical products.

The compositions may contain from 0.1% by weight, preferably from 10-60%, or more, by weight, of the antibody of the invention, depending on the method of administration.

It will be recognized by one of skill in the art that the optimal quantity and spacing of individual dosages of an antibody of the invention will be determined by the nature and extent of the disease or condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

FIG. 1 shows neutralisation of human IL-1β signalling with recombinant antibodies 97 and 100. Neutralization (reduction in luminescence) of IL-1β by increasing concentrations of antibody 97 is shown by the closed diamonds, by increasing concentrations of antibody 100 by closed squares. Controls were included: the open circle shows background luminescence, the open triangle shows luciferase production in the presence of 3 pg/ml IL-1β alone, the open square shows luciferase production in the presence of 15 pg/ml IL-1β alone, and the open diamond shows luciferase production in the presence of 30 pg/ml IL-1β alone.

Preferred features of each embodiment of the invention are as for each of the other embodiments mutatis mutandis. All publications, including but not limited to patents and patent applications cited in this specification are herein incorporated by reference as if each individual publication were specifically and individually indicated to be incorporated by reference herein as though fully set forth.

The invention will now be described with reference to the following experimental section, which is merely illustrative and should not in any way be construed as limiting the scope of the present invention.

EXPERIMENTAL

Positive Selection of Antigen-Specific B Cells by Flow Cytometry

Immunisation

Five Sprague Dawley Rats were immunised with 10 µg recombinant human IL-1β (Peprotech #200-01B) in 200 µl, 50:50 complete Freund's adjuvant and Sterile PBS. The animals were then boosted at week 4 and week 7 with 15 µg recombinant human IL-1β in 200 µl, 50:50 incomplete Freund's adjuvant and Sterile PBS. A test bleed was taken for each of the animals and the sera was assayed for human IL-1β neutralising activity (see below). The animals were then boosted a further three times at approximately 4 weekly intervals with 15 µg recombinant human IL-1β in 200 µl, 50:50 incomplete Freund's Adjuvant and Sterile PBS. Two weeks after the last boost, blood and spleens were harvested.

Preparation of Rat Lymphocytes and Splenocytes (The Populations for Enrichment)

Lymphocytes were separated from whole blood by firstly diluting the samples at approximately 1:10 in sterile PBS. Then 8 ml of diluted blood was layered onto 5 ml of Mammalian Lympholyte® (Cedarlane Laboratories Ltd. #CL5120) in 15 ml Falcon tubes. The samples were then centrifuge at 800 g for 20 min giving a well-defined, white lymphocyte layer at the interface between the liquids. This lymphocyte containing band and the upper 'blood plasma' containing layer were transferred into a new 15 ml falcon tube and centrifuged at 800 g for 10 min to pellet the lymphocytes. The supernatant was collected and stored at 4° C. for future use, whilst the cells were washed 3 times in immune medium (RPMI, 10% FCS, 2% HEPES, 1% Glutamine, and 1× Pen/Strep). Following the final wash the cells were frozen in 90% FCS and 10% DMSO and stored in liquid nitrogen until use.

Individual rat spleens were transferred into warmed immune media and cut into small pieces. The pieces were pushed through a mesh strainer to disperse the splenocytes. These were pelleted by centrifugation, the supernatant was removed and the cells washed thoroughly in immune media The cell pellets were frozen in 90% FCS and 10% DMSO aliquots and stored in liquid nitrogen until use.

Protein G Purification of Anti-Human IL-1β IgG from Rat Serum and Plasma

A pool of a total of 44 ml of plasma and serum from three of the immunised rats was used to prepare an IgG fraction for labelling with Alexa Fluor 488 dye. The serum/plasma pool volume was made up to 100 ml with PBS and passed through a protein G column (18 ml) with a minimum contact time with the Protein G beads of 20 min/ml of the pool. Following loading the column was washed with 5-10 column volumes of PBS. IgG was eluted in 0.1M glycine-HCl, pH 2.7 and neutralised using 2M Tris-HCl, pH 8.5 immediately. The IgG pool was concentrated and diafiltered into PBS using an Amicon stirred cell (Millipore, Cat. No. YM1013632).

Purification and Labelling of Polyclonal Rat Anti-Human IL-1β

A total of 30 µl of 10 mM Alexa Fluor 488 O-succinimide ester (Molecular Probes Inc. Product No. 20000) in dry DMSO (Perbio Science UK Ltd) was added dropwise approximately 1 ml of IgG (4.5 mg total) with vortexing. The reaction was allowed to proceed in the dark at 37° C. for 3 hr. The reaction mixture was separated by application to a PD10 column (Amersham Biosciences) in PBS (the PD10 column was prepared by blocking with 20% PEG, 20000 MW followed by equilibration in PBS).

Cell Labelling

An aliquot of splenocytes from the human IL-1β immunised rats was recovered from liquid nitrogen storage, transferred into 10 ml of warmed immune media, centrifuged and washed in immune media before being transferred into a T175 tissue culture flask in 60 ml immune media. The splenocytes were cultured overnight (16 hr) at 37° C. to deplete all adherent cell types from the cell mix. Cells that remained in suspension were counted and washed thoroughly in cold PBS before use.

Cell labelling was carried out in a 15 ml Falcon tube that had been blocked with blocking buffer (5% FCS, 0.1 mM EDTA in PBS) on ice at 4° C. for 30 min. A total of approximately $3 \times 10^7$ cells was incubated with 60 µg/ml Chrom-Pure™ rat IgG from normal rat sera (Jackson ImmunoResearch #012-000-003) and 17 ng/ml human IL-1β (Peprotech #200-01B) in blocking buffer for 1 hr on ice. Following this incubation the cells were washed 3 times with 15 ml ice-cold blocking buffer. After the final wash cells were resuspended in 5001 µl blocking buffer containing 2 µg/ml purified polyclonal rat anti human IL-1β conjugated with Alexa Fluor 488 and 100 µl PE-conjugated mouse anti-rat CD45RA (Serotech #MCA340PE), and incubated in the dark at 4° C. for 1 hr. The cells were then washed 3 times with 15 ml ice-cold blocking buffer. After the final wash the cells were resuspended to give a final concentration of $1 \times 10^7$ cells per ml in PBS containing 0.1 mM EDTA. The sample was passed through a cell filter (50 µm Syringe Filcons BD Bioscience #340603) to remove any debris or cell aggregates that may cause an obstruction during the flow cytometry.

FACS Analysis

FACS analysis and sorting was performed using a MoFlo® Cytomation and the Cytomation Summit software. A specific population of live cells stained with PE conjugated to the anti-rat CD45RA detected in the FL2 channel, which was also positively stained with FITC labelled anti-human IL-1β in the FL1 channel was identified. This double-labelled population represented a population enriched in B cells displaying surface IgG specific for human IL-1β.

Plating and Culture

The enriched population of cells was seeded at 5 cells per well across 12×96-well tissue culture treated plates already containing a B cell stimulating culture mix. This B cell stimulating culture mix consisted of 50,000 irradiated EL4.B5 cells and 4% rabbit TSN (rabbit T cells stimulated culture supernatant) in a total volume of 200 µl per well. The cells were then cultured for 7 days before the culture supernatant was assayed for human IL-1β specific antibody secretion.

Screening-Primary ELISA Screen

An ELISA screen of the culture supernatant was used to identify the wells that contained B cells secreting anti-human IL-1β specific antibodies. The assays were carried out in 12×96-well Nunc Maxisorp plates (Fisher #DIS-971-010P) coated overnight at 4° C. with 50 µl/well of 1 µg/ml polyclonal goat anti-human IL-1β in coating buffer (50 mM Sodium Bicarbonate, pH 9.6). The coating buffer was removed and 50 µl of 500 ng/ml hIL-1β made up in PEG blocking buffer (1% PEG 20000 MW, 0.1% Tween in PBS) was added to each of the wells and the plates were incubated for 1 hr at room temperature. Following this incubation the wells were washed 3 times with wash buffer (PBS containing 0.1% Tween 20). The plates were then blocked with 100 µl PEG blocking buffer for 1 hr at room temperature before being washed 3 more times in wash buffer. The 40 µl of PEG blocking buffer was added to each of the wells before adding 10 µl of culture supernatant from the B cell culture plates. The assay was then allowed to incubate for 1 hr at room temperature. The wells were then washed 3 times with wash buffer before adding 50 µl peroxidase conjugated goat F(ab')$_2$ anti-rat IgG Fcγ specific antibody (Jackson ImmunoResearch #112-036-071) diluted 1:3000 in PEG blocking buffer. The plates were once again incubated for 1 hr at room temperature before being washed 3 times with wash buffer. Finally, 100 µl TMB (Roche #784974) substrate was added to each of the wells and the colourless to blue colour change revealed positive wells. The plates were then read on the Multiskan (Labsystems) plate reader, using the Ascent software at 630/490 mn, for data analysis. In particular, two positive antibodies were selected for neutralising ability (see below).

Neutralisation Assay—Biacore Analysis of Antibody Blocking of IL-1β/Receptor Docking BIA (Biomolecular Interaction Analysis) was performed using a BIAcore 2000 (BIAcore AB). Immobilised anti-rat IgG, Fc fragment specific (Jackson ImmunoResearch) captured IgG from a 40 µl injection of culture supernatant at a flow rate of 10 µl/min in HBS-EP buffer. For the kinetic analysis human IL1β was titrated over the captured antibody at various concentrations. Results are shown in Table 1. The sensorgrams for IL-1β binding were double referenced by using a blocked flow cell and a buffer blank. Kinetic parameters were calculated using BIA evaluation 2.1, 3.0 or 3.1 software.

TABLE 1

| Sample | Ka $e^5$ | Kd $e^{-5}$ | KD pM |
|---|---|---|---|
| 97 | 3.9 | 3.27 | 83.8 |
| 100 | 3.61 | 3.05 | 84.5 |

Specific Antibody Gene Cloning

B cells from positive wells identified following the primary ELISA screen which were specific for IL-1β that also showed potential neutralising activity on the Biacore screen were selected for cloning. For this step the entire contents of the well was harvested and washed in PBS before being pelleted and resuspended into 15 μl of PBS. The cell sample was then split in 3 μl aliquots and transferred to 0.5 ml PCR tubes. cDNA was prepared by reverse transcription using a Superscript™ III Reverse Transcriptase kit (Invitrogen cat. #18080-044) in a 20 μl total volume. Primary PCR fragments were prepared by adding 2 μl of the reverse transcription reaction and the appropriate primary primers in conjunction with a TaqPlus Precision PCR system (Stratagene cat. #600211) in a total volume of 50 μl as described below. A secondary PCR reaction was performed with 2 μl of the primary PCR product, the appropriate secondary primers in conjunction with Precision PCR buffer, dNTPs and TaqPlus Precision in a total volume of 50 μl as described below.
Thermal Cycler Programs:
Reverse Transcription

| | | |
|---|---|---|
| 1. | 50° C. | 60 minutes |
| 2. | 70° C. | 15 minutes |

Primary PCR

| | | |
|---|---|---|
| 1. | 94° C. | 3 minutes |
| 2. | 94° C. | 30 seconds |
| 3. | 50° C. | 30 seconds |
| 4. | 72° C. | 1 minute |
| 5. | go to step 2 | 40 cycles total |
| 6. | 72° C. | 5 minutes |
| 7. | 4° C. | hold |

Secondary Nested PCR

| | | |
|---|---|---|
| 1. | 94° C. | 3 minutes |
| 2. | 94° C. | 30 seconds |
| 3. | 55° C. | 30 seconds |
| 4. | 72° C. | 1 minute |
| 5. | go to step 2 | 40 cycles total |
| 6. | 72° C. | 5 minutes |
| 7. | 4° C. | hold |

The PCR fragments were purified using Qiagen's Qiaquick 8 PCR purification kit (catalogue No. 28144) and eluted in 80 μl elution buffer. The heavy chain variable fragments were digested with XhoI and HindIII and ligated into the corresponding sites of the expression vector phFabHC (mammalian expression construct containing human γ1 CH1). The kappa light chain fragments were digested with BsiWI and HindIII and ligated into the corresponding sites of expression vector pMR10-HS (mammalian expression construct containing human Cκ). This results in the formation of heavy and light chain rat-human chimeric antibody genes. 4×VH and 4×VL clones (plasmid DNA from individual transformed colonies) from each cell pellet aliquot were sequenced. Consensus sequences were identified and pairs of relevant clones were used for transient expression in CHO cells.
Expression in Mammalian Cells Monolayers of CHO cells in 6-well plates ($1.2 \times 10^6$ cells/well) were transfected with 2 μg each of heavy and light chain plasmid DNA using Invitrogen's Lipofectamine 2000 (catalogue No. 11668-019) transfection reagent according to the manufacturer's instructions. The cells were incubated for 5 days at 37° C., then the culture supernatants were harvested and assayed for the presence of Fab, their ability to neutralize human IL-1 and their binding affinity for human IL-1β (Biacore analysis, as described above).
Anti-1β Reporter Gene Bioassay A549 cells which had been stably transfected with the E-selectin promoter linked to the luciferase gene (hereinafter referred to as A549-ES-Luc cells) were grown in RPMI 1640 (phenol-free) containing 10% FCS, 2 mM Glutamine and 1 mg/ml G418. These A549-ES-Luc cells express IL-1RI receptors. Cells were plated out into white opaque 96-well plates (Packard) at 15,000 cells/well and allowed to adhere overnight at 37° C./5% CO2. Samples for assay were set up in individual assay tubes, each tube containing culture supernatant (from transfected CHO cells, above) or control culture supernatant (untransfected CHO cell growth medium). Each tube additionally contained recombinant human IL-1β (Preprotech) at a final concentration of 30 pg/ml. Tubes were incubated for 30 minutes at room temperature. A549-ES-Luc growth media was removed and replaced with 100 μl of the room temperature incubate. Cells were incubated for 4 hours at 37° C. in 5% $CO_2$. Control wells that did not contain IL-1β ere included to allow the correction for basal luciferase activity in these cells. Luciferase expression was then assayed using a luciferase reporter gene assay kit (LucLite from Packard). FIG. 1 shows the results of the neutralisation of IL-1RI signalling by the transiently expressed antibodies, numbers 97 and 100. Both antibodies neutralised IL-1RI signalling as shown by the loss of luciferase production with increasing antibody concentration.

The invention claimed is:

1. A method of enriching a population of cells in those cells which produce an antibody that recognises an antigen of interest wherein the population of cells is derived from one or more animal immunised with an untagged antigen of interest, and wherein an unlabelled antigen of interest is used in conjunction with a labelled polyclonal antibody that recognizes said antigen of interest, wherein the population of cells is enriched by:
   a) bringing said population into contact with an antibody that recognises a marker which is essentially unique to those cells present in a population which are capable of producing an antibody, said antibody that recognises a marker being attached to a first fluorescent label;
   b) bringing said population into contact with the antigen of interest, which is unlabelled;
   c) bringing said population into contact with a sample comprising a polyclonal antibody that recognises said antigen, said polyclonal antibody being attached to a second fluorescent label and wherein said polyclonal antibody is prepared from a sample of blood from said immunised animal; and
   d) separating from the population those cells which are detectable by virtue of being associated with the first and second fluorescent labels.

2. The method of claim 1, wherein parts a) and c) are performed simultaneously and the performance comprises at least one wash step.

3. The method of claim 1, wherein the separation of the cells producing an antibody that recognises the antigen of interest is performed using fluorescence activated cell sorting.

4. A method of enriching a population of cells in those cells which produce an antibody that recognises an antigen of interest, and wherein an unlabelled antigen of interest is used in conjunction with a labelled polyclonal antibody that recognizes said antigen of interest, wherein the population of cells is enriched by:

a) bringing said population into contact with an antibody that recognises a marker which is essentially unique to those cells present in the population which are capable of producing an antibody, said antibody that recognises a marker being attached to a first fluorescent label;
b) bringing said population into contact with the antigen of interest which is unlabelled;
c) bringing said population into contact with a sample comprising a polyclonal antibody that recognises said antigen, said polyclonal antibody being attached to a second fluorescent label; and
d) separating from the population those cells which are detectable by virtue of being associated with the first and second fluorescent labels wherein part (b) is performed before parts (a) and (c) and wherein part (b) is followed by a washing step.

5. A method of claim 4, wherein the population of cells is derived from an animal immunised with an untagged antigen of interest.

* * * * *